United States Patent [19]

Thiele

[11] 4,146,387
[45] Mar. 27, 1979

[54] SYNERGISTIC HERBICIDAL COMPOSITIONS

[75] Inventor: Gerald H. Thiele, Sunnyvale, Calif.

[73] Assignee: Stauffer Chemical Company, Westport, Conn.

[21] Appl. No.: 854,559

[22] Filed: Nov. 25, 1977

[51] Int. Cl.² .............................................. A01N 9/20
[52] U.S. Cl. ........................................ 71/118; 71/111
[58] Field of Search ........................................ 71/118

[56] References Cited

U.S. PATENT DOCUMENTS

| | | | |
|---|---|---|---|
| 3,272,844 | 9/1966 | Easton et al. | 260/347.3 |
| 3,457,156 | 10/1969 | Olin | 71/118 |
| 3,547,620 | 12/1970 | Olin | 71/118 |
| 3,557,209 | 1/1971 | Richter et al. | 260/559 |
| 4,022,611 | 5/1977 | Vogel | 71/118 |

*Primary Examiner*—Catherine L. Mills
*Attorney, Agent, or Firm*—M. Henry Heines

[57] ABSTRACT

Synergistic herbicidal activity is displayed by compositions comprising the following two components:

(1) an amide of the formula

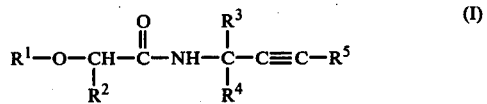

in which
R¹ is substituted phenyl, with one to three substituents independently selected from the group consisting of chlorine, bromine, iodine, or $C_1$-$C_4$ alkyl,
$R^2$, $R^3$, and $R^4$ are independently $C_1$-$C_4$ alkyl, and,
$R^5$ is hydrogen or $C_1$-$C_4$ alkyl, and (2) a haloacetanilide of the formula

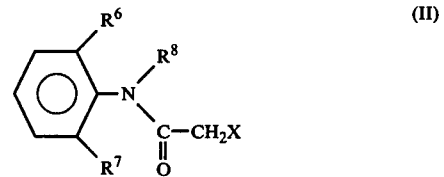

in which
$R^6$ and $R^7$ are independently selected from the group consisting of hydrogen and $C_1$-$C_6$ alkyl,
$R^8$ is a member selected from the group consisting of $C_1$-$C_6$ alkyl, $C_3$-$C_6$ alkenyl, $C_3$-$C_6$ alkynyl, -$R^9$-O-$R^{10}$, and

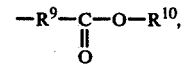

in which $R^9$ is $C_1$-$C_8$ alkylene and $R^{10}$ is $C_1$-$C_6$ alkyl, and
X is chlorine, bromine, or iodine.

26 Claims, No Drawings

SYNERGISTIC HERBICIDAL COMPOSITIONS

DESCRIPTION OF THE INVENTION

This invention relates to synergistic herbicidal compositions.

It has been discovered that synergism in the control of undesired vegetation is exhibited by compositions comprising the following two components:

(1) an amide of the formula

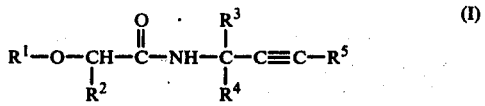

in which $R^1$ is substituted phenyl, with one to three substituents independently selected from the group consisting of chlorine, bromine, iodine, or $C_1$-$C_4$ alkyl, $R^2$, $R^3$, and $R^4$ are independently $C_1$-$C_4$ alkyl, and $R^5$ is hydrogen or $C_1$-$C_4$ alkyl, and (2) a haloacetanilide of the formula

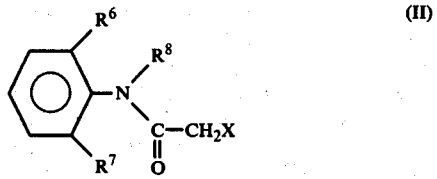

in which $R^6$ and $R^7$ are independently selected from the group consisting of hydrogen and $C_1$-$C_6$ alkyl, $R^8$ is a member selected from the group consisting of $C_1$-$C_6$ alkyl, $C_3$-$C_6$ alkenyl, $C_3$-$C_6$ alkynyl, -$R^9$-O-$R^{10}$, and

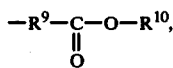

in which $R^9$ is $C_1$-$C_8$ alkylene and $R^{10}$ is $C_1$-$C_6$ alkyl, and

X is chlorine, bromine or iodine.

Within the scope of the above-defined general formulae, certain embodiments are preferred, as indicated below:

In Formula I, $R^1$ is preferably substituted phenyl, with one to three substituents independently selected from the group consisting of chlorine and methyl; more preferably phenyl disubstituted by chlorine or methyl; and most preferably 3,5-dichlorophenyl or 3,5-dimethylphenyl;

$R^2$, $R^3$, and $R^4$ are preferably independently selected from the group consisting of methyl and ethyl; and $R^5$ is preferably hydrogen or methyl.

In Formula II, $R^6$ and $R^7$ are independently selected from the group consisting of hydrogen, methyl and ethyl;

$R^8$ is preferably selected from the group consisting of $C_1$-$C_6$ alkyl, -$R^9$-O-$R^{10}$, and

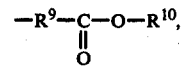

in which $R^9$ is $C_1$-$C_3$ alkylene and $R^{10}$ is $C_1$-$C_3$ alkyl; most preferably selected from the group consisting of $C_1$-$C_3$ alkyl and -$R^9$-O-$R^{10}$ in which $R^9$ is $C_1$-$C_3$ alkylene and $R^{10}$ is methyl; and X is preferably chlorine.

The terms "alkyl" and "alkylene" as used herein are intended to include both straight- and branched-chain groups. All carbon atom ranges are intended to be inclusive of both upper and lower limits.

The term "herbicide", as used herein, means a compound which controls or modifies the growth of plants. By the term "herbicidally effective amount" is meant an amount of compound which causes a modifying effect upon the growth of plants. By "plants" is meant germinant seeds, emerging seedlings and established vegetation, including roots and above ground portions. Such modifying effects include all deviations from natural development, for example, killing, retardation, defoliation, desiccation, regulation, stunting, tillering, stimulation, leaf burn, dwarfing and the like.

The term "synergism" is employed in its traditional sense and describes a herbicidal effect of a composition containing two or more active herbicidal compounds which is greater than the sum of the herbicidal effects of the individual compounds when used alone.

The amides of the present compositions are known herbicides and can be prepared by the procedures described in U.S. Pat. No. 3,272,844. Examples of such amides are N-(1,1-dimethyl-2-propynyl)-α-(4-bromophenoxy) butyramide, N-(1,1-dimethyl-2-butynyl)-α-(3,5-dichlorophenoxy) butyramide, N-(1,1-dimethyl-2-butynyl)-α-(3,5-dimethylphenoxy) butyramide, and N-(1,1-dimethyl-2-propynyl)-α-(3,5-dichlorophenoxy) butyramide.

The haloacetanilides of the present compositions are also known herbicides and can be prepared by the procedures described in U.S. Pat. Nos. 2,863,752, 3,442,945, 4,022,611 and 4,032,657. Examples of such haloacetanilides are N-[3'-methoxypropyl-(2)]-2-methyl-6-ethyl chloroacetanilide, N-isopropylchloroacetanilide, N-(methoxymethyl)-2,6-diethyl chloroacetanilide, N-(2'-methoxyethyl)-2,6-dimethyl chloroacetanilide, N-(2'-methoxyethyl)-2,6-dimethyl chloroacetanilide, and N-(2'-methylcarbethoxy)-2,6-diethyl chloroacetanilide.

The amide and haloacetanilide herbicides are used in a weight ratio of amide to haloacetanilide of 0.001–50:1, preferably 0.01–10:1, and most preferably 0.01–8:1.

The synergistic herbicidal compositions of this invention can be prepared by any conventional method. It is preferred to use herbicidal components in the form of wettable powders or emulsifiable concentrates. Amounts of each component are added to sufficient water to provide the desired rate of application of active ingredient. The compositions of this invention are generally employed at a rate of 0.01 to 50 pounds per acre, preferably 0.1 to 25 pounds per acre. The amount used will depend on the weeds to be controlled and the degree of control desired.

Herbicidal compositions illustrative of those embodied in the instant application were prepared and synergistic effect evaluated in the following examples.

EXAMPLES

The compositions of the present invention were tested for herbicidal activity and synergism by a pre-emergence surface application procedure, conducted as follows:

Fiber flats which were 6 inches wide, 10 inches long, and 2½ inches deep were filled to a depth of about 2¼ inches with sandy loam soil of moisture content approximately 9%, containing 75 parts per million (ppm) of cis-N[(trichloromethyl)thio]-4-cyclohexene-1,2-dicarboximide (a commercial fungicide) and 50 ppm of 17-17-17 fertilizer (17% N, 17% $P_2O_5$, and 17% $K_2O$ on weight basis). The soil was leveled and a row marker was used to impress seven rows across the width of the flat. In each flat, seeds of each of the following weeds were planted, with one full row for each seed type:

TABLE I

| Plant Species Tested | |
|---|---|
| COMMON NAME | SCIENTIFIC NAME |
| pigweed | *Amaranthus retroflexus* |
| foxtail | *Setaria sp.* |
| watergrass | *Echinocloa crusgalli* |
| annual morning glory | *Ipomoea purpurea* |
| nightshade | *Solanum sp.* |
| mustard | *Brassica juncea* |
| velvet leaf | *Abultilon theophrasti* |

The flats were then treated by atomizing a measured amount of stock solution evenly over the soil surface. For each compound applied singly, 5 milliliters (ml) of stock solution selected from Table II for the appropriate application rate was used per flat. For compounds applied in combination, a mixture was used consisting of 5 ml each of the appropriate stock solutions selected from the table.

TABLE II

| | Stock Solutions | | | |
|---|---|---|---|---|
| | Quantity dissolved in mixture of 50 ml acetone and 50 ml water | | | |
| | Application Rate: | | | |
| Amides* | ⅛lb/A | ¼lb/A | ½lb/A | |
| No. 1 | 10 mg | 20 mg | 40 mg | |
| No. 2 | 10 mg | 20 mg | 40 mg | |
| No. 3 | 10 mg | 20 mg | 40 mg | |
| | Quantity dissolved in mixture of 100 ml water | | | |
| | Application Rate: | | | |
| Haloacetanilides* | ⅛lb/A | ¼lb/A | ½lb/A | 1 lb/A |
| DUAL®6E | 13 mg | 27 mg | 53 mg | — |
| LASSO®4E | — | 42 mg | 83 mg | 167 mg |
| RAMROD® 65 WP | — | 31 mg | 62 mg | 123 mg |

*Compound identification:
Amides:
No. 1: N-(1,1-dimethyl-2-butynyl)αN-(1,1,-dimethyl-2-butynyl)-α-(3,5-dichlorophenoxy) butyramide
No. 2: N-(1,1-dimethyl-2-butynyl)-α-(3,5-dimethylphenoxy) butyramide
No. 3: N-(1,1-dimethyl-2-propynyl)-α-(3,5-dichlorophenoxy) butyramide
Haloacetanilides (active ingredient followed by percent present in formulation):
DUAL® 6E : N-8 3'-methoxypropyl-(2)]-2-methyl-6-ethyl chloroacetanilide (75%)
LASSO® 4E : N-methoxymethyl-2,6-diethyl chloroacetanilide (ALACHLOR) (48%)
RAMROD® 65 WP : N-isopropyl chloroacetanilide (PROPACHLOR) (65%)

Following treatment, the flats were placed in a greenhouse for three weeks and five days at 70°–85° F. where they were watered daily. At the end of this period, the degree of weed control was estimated and recorded as percent control compared to the same species in an untreated check flat of the same age.

The percentage control is based on the total injury to the plants due to all factors including inhibited germination, killing of the plant tissue after emergence, stunting, malformation, chlorosis and other types of injury. The control ratings vary from 0 to 100% where 0 represents no effect with growth equal to the untreated control, and 100 represents complete kill.

The results of each test are reported in Tables III, IV, and V in the columns headed by the symbol "O" (indicating observed result). These results were then compared with the expected result, shown in the columns headed by the symbol "E", derived from Limpel's formula (Limpel et al., 1962, "Weed Control by Dimethylchloroterephthalate Alone and in Certain Combinations," Proc. NEWCC, Vol. 16, pp. 48–53):

$$E = X + Y - \frac{XY}{100}$$

where
X = observed percent injury when one of the herbicides is used alone, and
Y = observed percent injury when the other herbicide is used alone.

The relationship between the observed result and the expected result for each combination of amide and haloacetanilide tested is indicated in the columns headed by the symbol "R." When the observed result exceeds the expected result, synergism has been shown, which is represented by the symbol "S." When the observed result is less than the expected result, there is antagonism between the herbicides, represented by the symbol "A." When the observed result equals the expected result, the relationship of the herbicides in the combination is merely additive, as represented by the symbol "Ad."

TABLE III

Percent Control Using N-(1,1-Dimethyl-2-butynyl-α-(3,5-dichlorophenoxy) butyramide A. In combination with DUAL® 6E

| lb/A Amide | lb/A DUAL | Pigweed | | | Foxtail | | | Annual morning glory | | | Nightshade | | | Mustard | | | Velvet leaf | | |
|---|---|---|---|---|---|---|---|---|---|---|---|---|---|---|---|---|---|---|---|
| | | O | E | R | O | E | R | O | E | R | O | E | R | O | E | R | O | E | R |
| ⅛ | — | 10 | | | 40 | | | 10 | | | 80 | | | 40 | | | 0 | | |
| ¼ | — | 20 | | | 85 | | | 20 | | | 90 | | | 75 | | | 0 | | |
| ½ | — | 30 | | | 100 | | | 60 | | | 100 | | | 80 | | | 10 | | |
| — | ⅛ | 0 | | | 65 | | | 0 | | | 20 | | | 0 | | | 0 | | |
| — | ¼ | 0 | | | 95 | | | 0 | | | 40 | | | 0 | | | 10 | | |
| — | ½ | 0 | | | 100 | | | 20 | | | 60 | | | 20 | | | 20 | | |
| ⅛ | ⅛ | 20 | 10 | S | 95 | 79 | S | 20 | 10 | S | 90 | 84 | S | 50 | 40 | S | 10 | 0 | S |
| ¼ | ¼ | 30 | 10 | S | | | | 20 | 10 | S | 95 | 88 | S | 50 | 40 | S | 20 | 10 | S |
| ½ | ½ | 30 | 10 | S | | | | 30 | 28 | S | 98 | 92 | S | 60 | 52 | S | 30 | 20 | S |

TABLE III-continued

| | | | | | | | | | | | | | | | | | | |
|---|---|---|---|---|---|---|---|---|---|---|---|---|---|---|---|---|---|---|
| ¼ | ¼ | 20 | 20 | Ad | | 30 | 20 | S | | | | 70 | 75 | A | 10 | 0 | S |
| ¼ | ½ | 75 | 20 | S | | 65 | 20 | S | | | | 80 | 75 | S | 50 | 10 | S |
| ¼ | 1 | 98 | 20 | S | | 80 | 36 | S | | | | 98 | 80 | S | 65 | 20 | S |
| ½ | ¼ | 50 | 30 | S | | 75 | 60 | S | | | | 90 | 80 | S | 40 | 10 | S |
| ½ | ½ | 60 | 30 | S | | 80 | 60 | S | | | | 90 | 80 | S | 50 | 19 | S |
| ½ | 1 | 100 | 30 | S | | 85 | 68 | S | | | | 95 | 84 | S | 50 | 28 | S |

B. In combination with LASSO®4E

| lb/A Amide | lb/A LASSO | | | | | | | | | | | | | | | | | |
|---|---|---|---|---|---|---|---|---|---|---|---|---|---|---|---|---|---|---|
| — | ¼ | 40 | | | 100 | 0 | | | 10 | | | 0 | | | 20 | | |
| — | ½ | 60 | | | 100 | 10 | | | 20 | | | 20 | | | 40 | | |
| — | 1 | 90 | | | 100 | 20 | | | 30 | | | 40 | | | 50 | | |
| ⅛ | ¼ | 90 | 46 | S | | 20 | 10 | S | 90 | 82 | S | 20 | 40 | A | 30 | 20 | S |
| ⅛ | ½ | 100 | 64 | S | | 30 | 19 | S | 95 | 84 | S | 30 | 52 | A | 50 | 40 | S |
| ⅛ | 1 | 100 | 91 | S | | 40 | 28 | S | 98 | 86 | S | 40 | 64 | A | 60 | 50 | S |
| ¼ | ¼ | 100 | 52 | S | | 30 | 20 | S | 90 | 91 | A | 30 | 75 | A | 50 | 20 | S |
| ¼ | ½ | 100 | 68 | S | | 40 | 28 | S | 95 | 92 | S | 40 | 80 | A | 50 | 40 | S |
| ¼ | 1 | 100 | 92 | S | | 90 | 36 | S | 98 | 93 | S | 60 | 85 | A | 60 | 50 | S |
| ½ | ¼ | 100 | 58 | S | | 95 | 60 | S | | | | 95 | 80 | S | 60 | 28 | S |
| ½ | ½ | 100 | 72 | S | | 98 | 64 | S | | | | 98 | 84 | S | 70 | 46 | S |
| ½ | 1 | 100 | 93 | S | | 98 | 68 | S | | | | 98 | 88 | S | 80 | 55 | S |

C. In combination with RAMROD® 65 WP

| lb/A Amide | lb/A RAMROD | Pigweed | | | Foxtail | | | Annual morning glory | | | Nightshade | | | Mustard | | | Velvet leaf | | |
|---|---|---|---|---|---|---|---|---|---|---|---|---|---|---|---|---|---|---|---|
| | | O | E | R | O | E | R | O | E | R | O | E | R | O | E | R | O | E | R |
| — | ¼ | 0 | | | 100 | 0 | | | 10 | | | 10 | | | 30 | | |
| — | ½ | 10 | | | 100 | 0 | | | 10 | | | 10 | | | 40 | | |
| — | 1 | 10 | | | 100 | 10 | | | 20 | | | 20 | | | 50 | | |
| ⅛ | ¼ | 50 | 10 | S | | 20 | 10 | S | 90 | 82 | S | 0 | 46 | A | 40 | 30 | S |
| ⅛ | ½ | 60 | 19 | S | | 90 | 10 | S | 98 | 82 | S | 0 | 46 | A | 50 | 40 | S |
| ⅛ | 1 | 70 | 19 | S | | 95 | 19 | S | 98 | 84 | S | 0 | 52 | A | 60 | 50 | S |
| ¼ | ¼ | 90 | 20 | S | | 40 | 20 | S | 95 | 91 | S | 0 | 78 | A | 40 | 30 | S |
| ¼ | ½ | 90 | 28 | S | | 60 | 20 | S | 95 | 91 | S | 0 | 78 | A | 50 | 40 | S |
| ¼ | 1 | 95 | 28 | S | | 65 | 28 | S | 98 | 92 | S | 0 | 80 | A | 60 | 50 | S |
| ½ | ¼ | 80 | 30 | S | | 90 | 60 | S | | | | 95 | 82 | S | 60 | 37 | S |
| ½ | ½ | 80 | 37 | S | | 95 | 60 | S | | | | 98 | 82 | S | 65 | 46 | S |
| ½ | 1 | 90 | 37 | S | | 98 | 64 | S | | | | 98 | 84 | S | 70 | 55 | S |

On foxtail, watergrass, and nightshade tests, both observed and expected results were too close to 100% for synergism evaluation, except as indicated.

TABLE IV

Percent Control Using N-(1,1-Dimethyl-2-butyl-α-(3,5-dimethylphenoxy)butyramide

A. In combination with DUAl®6E

| lb/A Amide | lb/A DUAL | Pigweed | | | Foxtail | | | Annual morning glory | | | Nightshade | | | Mustard | | | Velvet leaf | | |
|---|---|---|---|---|---|---|---|---|---|---|---|---|---|---|---|---|---|---|---|
| | | O | E | R | O | E | R | O | E | R | O | E | R | O | E | R | O | E | R |
| ⅛ | — | 40 | | | 0 | | | 10 | | | 60 | | | 10 | | | 0 | | |
| ¼ | — | 60 | | | 20 | | | 30 | | | 98 | | | 20 | | | 0 | | |
| ½ | — | 80 | | | 30 | | | 30 | | | 98 | | | 30 | | | 20 | | |
| ⅛ | ⅛ | 40 | 40 | Ad | 100 | 65 | S | 20 | 10 | S | 98 | 68 | S | 20 | 10 | S | 10 | 0 | S |
| ⅛ | ¼ | 50 | 40 | S | | | | 30 | 10 | S | 98 | 76 | S | 20 | 10 | S | 20 | 10 | S |
| ⅛ | ½ | 60 | 40 | S | | | | 50 | 28 | S | 99 | 84 | S | 30 | 28 | S | 40 | 20 | S |
| ¼ | ⅛ | 60 | 60 | Ad | 100 | 72 | S | 40 | 30 | S | | | | 30 | 20 | S | 10 | 0 | S |
| ¼ | ¼ | 70 | 60 | S | | | | 60 | 30 | S | | | | 30 | 20 | S | 20 | 10 | S |
| ¼ | ½ | 80 | 60 | S | | | | 75 | 44 | S | | | | 40 | 36 | S | 30 | 20 | S |
| ½ | ⅛ | 40 | 80 | A | 100 | 76 | S | 60 | 30 | S | | | | 40 | 30 | S | 30 | 20 | S |
| ½ | ¼ | 60 | 80 | A | | | | 95 | 30 | S | | | | 50 | 30 | S | 40 | 28 | S |
| ½ | ½ | 100 | 80 | S | | | | 98 | 44 | S | | | | 60 | 44 | S | 50 | 36 | S |

B. In combination with LASSO®4E

| lb/A Amide | lb/A LASSO | | | | | | | | | | | | | | | | | |
|---|---|---|---|---|---|---|---|---|---|---|---|---|---|---|---|---|---|---|
| ⅛ | ¼ | 98 | 64 | S | | 20 | 10 | S | 100 | 64 | S | 20 | 10 | S | 40 | 20 | S |
| ⅛ | ½ | 100 | 76 | S | | 30 | 19 | S | 100 | 68 | S | 30 | 28 | S | 50 | 40 | S |
| ⅛ | 1 | 100 | 94 | S | | 40 | 28 | S | 100 | 72 | S | 50 | 46 | S | 60 | 50 | S |
| ¼ | ¼ | 100 | 76 | S | | 10 | 30 | A | | | | 30 | 20 | S | 30 | 20 | S |
| ¼ | ½ | 100 | 84 | S | | 40 | 37 | S | | | | 40 | 36 | S | 50 | 40 | S |
| ¼ | 1 | 100 | 96 | S | | 65 | 44 | S | | | | 65 | 52 | S | 60 | 50 | S |
| ½ | ¼ | 100 | 88 | S | | 50 | 30 | S | | | | 40 | 30 | S | 40 | 36 | S |
| ½ | ½ | 100 | 92 | S | | 60 | 37 | S | | | | 50 | 44 | S | 50 | 52 | A |
| ½ | 1 | 100 | 98 | S | | 95 | 44 | S | | | | 60 | 58 | S | 60 | 60 | Ad |

C. In combination with RAMROD® 65 WP

| lb/A Amide | lb/A RAMROD | Pigweed | | | Foxtail | | | Annual morning glory | | | Nightshade | | | Mustard | | | Velvet leaf | | |
|---|---|---|---|---|---|---|---|---|---|---|---|---|---|---|---|---|---|---|---|
| | | O | E | R | O | E | R | O | E | R | O | E | R | O | E | R | O | E | R |
| ⅛ | ¼ | 20 | 40 | A | | | | 10 | 10 | Ad | 100 | 64 | S | 20 | 19 | S | 30 | 30 | Ad |
| ⅛ | ½ | 30 | 46 | A | | | | 30 | 10 | S | 100 | 64 | S | 30 | 19 | S | 40 | 40 | Ad |
| ⅛ | 1 | 40 | 46 | A | | | | 30 | 19 | S | 100 | 68 | S | 40 | 28 | S | 60 | 50 | S |
| ¼ | ¼ | 70 | 60 | S | | | | 30 | 30 | Ad | | | | 0 | 28 | A | 30 | 30 | Ad |
| ¼ | ½ | 95 | 64 | S | | | | 40 | 30 | S | | | | 0 | 28 | A | 40 | 40 | Ad |
| ¼ | 1 | 98 | 64 | S | | | | 50 | 37 | S | | | | 0 | 36 | A | 50 | 50 | Ad |
| ½ | ¼ | 50 | 80 | A | | | | 95 | 30 | S | | | | 20 | 37 | A | 40 | 44 | A |
| ½ | ½ | 95 | 82 | S | | | | 98 | 30 | S | | | | 30 | 37 | A | 60 | 52 | S |

TABLE IV-continued

| | | | | | | | | | | | | | | |
|---|---|---|---|---|---|---|---|---|---|---|---|---|---|---|
| 1/8 | 1 | 98 | 82 | S | | 100 | 37 | S | | | 40 | 44 | A | 65 | 60 | S |

Observed results for DUAL® 6E, LASSO® 4E, and RAMROD® 65WP applied individually are listed in Table III.
On foxtail, watergrass, and nightshade tests, both observed and expected results were too close to 100% for synergism evaluation, except as indicated.

TABLE V

Percent Control Using N-(1,1-Dimethyl-2-propynyl)-α-(3,5-dichlorophenoxy) butyramide

A. In Combination with DUAl® 6E

| lb/A Amide | lb/A DUAL | Pigweed O | E | R | Foxtail O | E | R | Annual morning glory O | E | R | Nightshade O | E | R | Mustard O | E | R | Velvet leaf O | E | R |
|---|---|---|---|---|---|---|---|---|---|---|---|---|---|---|---|---|---|---|---|
| 1/8 | — | 10 | | | 20 | | | 0 | | | 70 | | | 10 | | | 0 | | |
| 1/4 | — | 60 | | | 50 | | | 0 | | | 90 | | | 10 | | | 0 | | |
| 1/2 | — | 95 | | | 100 | | | 20 | | | 95 | | | 20 | | | 0 | | |
| 1/8 | 1/2 | 50 | 10 | S | 100 | 72 | S | 10 | 0 | S | 80 | 76 | S | 10 | 10 | Ad | 10 | 0 | S |
| 1/4 | 1/2 | 60 | 10 | S | | | | 20 | 0 | S | 90 | 82 | S | 20 | 10 | S | 20 | 10 | S |
| 1/2 | 1/2 | 70 | 10 | S | | | | 30 | 20 | S | 95 | 88 | S | 40 | 28 | S | 30 | 20 | S |
| 1/8 | 1 | 70 | 60 | S | 100 | 83 | S | 10 | 0 | S | 98 | 92 | S | 10 | 10 | Ad | 10 | 0 | S |
| 1/4 | 1 | 80 | 60 | S | | | | 20 | 0 | S | | | | 40 | 10 | S | 20 | 10 | S |
| 1/2 | 1 | 90 | 60 | S | | | | 70 | 20 | S | | | | 50 | 28 | S | 40 | 20 | S |
| 1/8 | 2 | 95 | 95 | Ad | | | | 20 | 20 | Ad | | | | 30 | 20 | S | 10 | 0 | S |
| 1/4 | 2 | 95 | 95 | Ad | | | | 30 | 20 | S | | | | 30 | 20 | S | 20 | 10 | S |
| 1/2 | 2 | 98 | 95 | S | | | | 50 | 36 | S | | | | 50 | 36 | S | 30 | 20 | S |

B. In Combination with LASSO® 4E

| lb/A Amide | lb/A LASSO | Pigweed O | E | R | Foxtail O | E | R | Annual morning glory O | E | R | Nightshade O | E | R | Mustard O | E | R | Velvet leaf O | E | R |
|---|---|---|---|---|---|---|---|---|---|---|---|---|---|---|---|---|---|---|---|
| 1/8 | 1/2 | 95 | 46 | S | 10 | 0 | S | 90 | 73 | S | 20 | 10 | S | 20 | 20 | | Ad | | |
| 1/4 | 1/2 | 98 | 64 | S | 20 | 10 | S | 98 | 76 | S | 30 | 28 | S | 30 | 40 | | A | | |
| 1/2 | 1 | 100 | 91 | S | 30 | 20 | S | 100 | 79 | S | 50 | 46 | S | 60 | 50 | | S | | |
| 1/8 | 1/2 | 95 | 76 | S | 10 | 0 | S | 98 | 91 | S | 20 | 10 | S | 20 | 20 | | Ad | | |
| 1/4 | 1/2 | 98 | 84 | S | 20 | 10 | S | 98 | 92 | S | 30 | 28 | S | 30 | 40 | | A | | |
| 1/2 | 1 | | | | 60 | 20 | S | 98 | 93 | S | 60 | 46 | S | 60 | 50 | | S | | |
| 1/8 | 1/2 | | | | 40 | 20 | S | | | | 50 | 20 | S | 30 | 20 | | S | | |
| 1/4 | 1/2 | | | | 65 | 28 | S | | | | 60 | 36 | S | 40 | 40 | | Ad | | |
| 1/2 | 1 | | | | 70 | 36 | S | | | | 70 | 52 | S | 60 | 50 | | S | | |

C. In combination with RAMROD® 65WP

| lb/A Amide | lb/A RAMROD | Pigweed O | E | R | Foxtail O | E | R | Annual morning glory O | E | R | Nightshade O | E | R | Mustard O | E | R | Velvet leaf O | E | R |
|---|---|---|---|---|---|---|---|---|---|---|---|---|---|---|---|---|---|---|---|
| 1/8 | 1/2 | 20 | 10 | S | | | | 10 | 0 | S | 95 | 73 | S | 10 | 19 | A | 40 | 30 | S |
| 1/4 | 1/2 | 20 | 19 | S | | | | 10 | 0 | S | 95 | 73 | S | 20 | 19 | S | 50 | 40 | S |
| 1/2 | 1 | 30 | 19 | S | | | | 20 | 10 | S | 98 | 76 | S | 20 | 28 | A | 60 | 50 | S |
| 1/8 | 1/2 | 80 | 60 | S | | | | 30 | 0 | S | 98 | 91 | S | 20 | 19 | S | 50 | 30 | S |
| 1/4 | 1/2 | 85 | 64 | S | | | | 60 | 0 | S | 98 | 91 | S | 30 | 19 | S | 60 | 40 | S |
| 1/2 | 1 | 90 | 64 | S | | | | 60 | 10 | S | 100 | 92 | S | 30 | 28 | S | 65 | 50 | S |
| 1/8 | 1/2 | 100 | 95 | S | | | | 70 | 20 | S | | | | 20 | 28 | A | 60 | 30 | S |
| 1/4 | 1/2 | | | | | | | 80 | 20 | S | | | | 20 | 28 | A | 70 | 40 | S |
| 1/2 | 1 | | | | | | | 85 | 28 | S | | | | 30 | 36 | A | 75 | 50 | S |

Observed results for DUAL® 6E, LASSO® 4E, and RAMROD® 65WP applied individually are listed in Table III.
On pigweed, foxtail, watergrass, and nightshade tests, both observed and expected results were too close to 100% for synergism evaluation, except as indicated.

The compositions of the present invention are useful as herbicides in controlling the growth of undesirable vegetation by pre-emergence or post-emergence application to the locus where control is desired. The compositions are generally embodied in formulations suitable for convenient application. In general, such formulations will contain inert or occasionally active ingredients or diluent carriers in addition to the active compound. Examples of such ingredients or carriers are water, organic solvents, dust carriers, granular carriers, surface active agents, oil and water, water in oil emulsions, wetting agents, dispersing agents, and emulsifying agents. The herbicidal formulations generally take the form of dusts, wettable powders, granules, solutions, or emulsifiable concentrates.

Dusts are free-flowing powder compositions containing the herbicidal compound impregnated on a particulate carrier. The particle size of the carrier is usually in the range of from about 30 to 50 microns. Examples of suitable carriers are talc, bentonite, diatomaceous earth, and pyrophyllite. Anticaking and antistatic agents can be added, if desired. The composition generally contains up to 50% of active ingredient.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhdyric alcohols, in which the alcohol groups are free, omega-substituted polyethylene glycols of relatively long chain length. A list of surface active agents suitable for use in agriculture formulations can be found in *Pesticide Formulations* by Wade Van Valkenburg, Marcel Dekker, Inc., N.Y. 1973 at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, and the like.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifable concentrates consist of an oil solution of the herbicide along with an emulsifying agent. Prior to use the concentrate is diluted with water to form a suspended emulsion of oil droplets. the emulsifiers used are usually a mixture of anionic and nonionic surfactants. Other additives such as spreading agents and stickers can be included in the emulsifiable concentrate.

The formulations described above, employing phytotoxic or herbicidally effective amounts of the compositions described herein, are applied to the loci where control is desired in any conventional manner. The loci referred to above include soil, seeds, seedlings, and the actual plants. Dusts and liquid compositions can be applied by the use of powder dusters, boom and hand sprayers and spray dusters. The compositions can also be applied from airplanes as dusts or sprays because they are effective in very low dosages. In order to modify or control growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvants or in combination with any of the above-described adjuvants. Other phytotoxic compounds useful in combination with the above-described compositions include, for example, 2,4-dichlorophenoxyacetic acids, 2,4,5-trichlorophenoxyacetic acid, 2-methyl-4-chlorophenoxyacetic acid, and the salts, esters and amides thereof; triazine derivatives, such as 2,4-bis(3-methoxypropylamino)-6-methyl-thio-s-triazine; 2-chloro-4-ethylamino-6-isopropylamino-s-triazine, and 2-ethylamino-4-isopropylamino-6-methylmercapto-s-triazine, urea derivatives such as 3-(3,4-dichlorophenyl)-1,1-dimethyl urea, and acetamides such as N,N-diallyl-α-chloroacetamide, N-(α-chloroacetyl) hexamethyleneimine, and N,N-diethyl-α-bromoacetamide, and the like; benzoic acids such as 3-amino-2,5-dichlorobenzoic; S-ethyl-dipropyl-thiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

The amount of a composition of the present invention which constitutes a phytotoxic or herbicidally effective amount depends upon the nature of the seeds or plants to be controlled. The rate of application of active ingredient varies from about 0.01 to about 50 pounds per acre, preferably about 0.1 to about 25 pounds per acre with the actual amount used depending on the overall cost and the desired results. It will be readily apparent to one skilled in the art that compositions exhibiting lower herbicidal activity will require a higher dosage rate for the same degree of control than more active compounds.

What is claimed is:

1. A synergistic herbicidal composition comprising a mixture of
   (1) a herbicidally effective amount of an amide of the formula

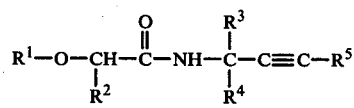

in which
R$^1$ is substituted phenyl, with one to three substituents independently selected from the group consisting of chlorine, bromine, iodine, or C$_1$-C$_4$ alkyl,
R$^2$, R$^3$, and R$^4$ are independently C$_1$-C$_4$ alkyl, and
R$^5$ is hydrogen or C$_1$-C$_4$ alkyl,
and
   (2) a herbicidally effective amount of a haloacetanilide of the formula

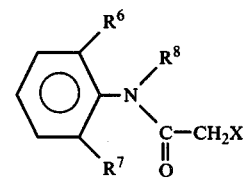

in which
R$^6$ and R$^7$ are independently selected from the group consisting of hydrogen and C$_1$-C$_6$ alkyl,
R$^8$ is a member selected from the group consisting of C$_1$-C$_6$ alkyl and -R$^9$-O-R$^{10}$, in which R$^9$ is C$_1$-C$_3$ alkylene and R$^{10}$ is C$_1$-C$_3$ alkyl, and
X is chlorine, bromine, or iodine, in a weight ratio of amide to haloacetanilide of 0.01-10:1.

2. A composition according to claim 1 in which R$^1$ is substituted phenyl, with one to three substituents independently selected from the group consisting of chlorine and methyl.

3. A composition according to claim 1 in which R$^1$ is 3,5-dichlorophenyl or 3,5-dimethylphenyl.

4. A composition according to claim 1 in which X is chlorine.

5. A composition according to claim 1 in which said amide is N-(1,1-dimethyl-2-butynyl)-α-(3,5-dichlorophenoxy) butyramide and said haloacetanilide is N-[(3'-methoxypropyl-(2)]2-methyl-6-ethyl chloroacetanilide.

6. A composition according to claim 1 in which said amide is N-(1,1-dimethyl-2-butynyl)-α-(3,5-dichlorophenoxy) butyramide and said haloacetamide is N-methoxymethyl-2,6-diethyl chloroacetanilide.

7. A composition according to claim 1 in which said amide is N-(1,1-dimethyl-2-butynyl)-α-(3,5-dichlorophenoxy) butyramide and said haloacetamide is N-isopropyl chloroacetanilide.

8. A composition according to claim 1 in which said amide is N-(1,1-dimethyl-2-butynyl)-α-(3,5-dimethylphenoxy) butyramide and said haloacetanilide is N-[3'-methoxy propyl-(2)]-2-methyl-6-ethyl chloroacetanilide.

9. A composition according to claim 1 in which said amide is N-(1,1-dimethyl-2-butynyl)-α-(3,5-dimethylphenoxy) butyramide and said haloacetanilide is N-methoxymethyl-2,6-diethyl chloroacetanilide.

10. A composition according to claim 1 in which said amide is N-(1,1-dimethyl-2-butynyl)-α-(3,5-dimethylphenoxy) butyramide and said haloacetanilide is N-isopropyl chloroacetanilide.

11. A composition according to claim 1 in which said amide is N-(1,1-dimethyl-2-propynyl)-α-(3,5-dichlorophenoxy) butyramide and said haloacetanilide is N-[3'-methoxypropyl-(2)]-2-methyl-6-ethyl chloroacetanilide.

12. A composition according to claim 1 in which said amide is N-(1,1-dimethyl-2-propynyl)-α-(3,5-dichlorophenoxy) butyramide and said haloacetanilide is N-methoxymethyl-2,6-diethyl chloroacetanilide.

13. A composition according to claim 1 in which said amide is N-(1,1-dimethyl-2-propynyl)-α-(3,5-dichlorophenoxy) butyramide and said haloacetanilide is N-isopropyl chloroacetanilide.

14. A method of controlling undesired vegetation which comprises applying to the locus where control is desired a synergistic herbicidal composition comprising a mixture of (1) a herbicidally effective amount of an amide of the formula

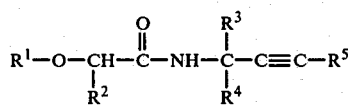

in which $R^1$ is substituted phenyl, with one to three substituents independently selected from the group consisting of chlorine, bromine, iodine, or $C_1$–$C_4$ alkyl, $R^2$, $R^3$, and $R^4$ are independently $C_1$–$C_4$ alkyl, and $R^5$ is hydrogen or $C_1$–$C_4$ alkyl, and (2) a herbicidally effective amount of a haloacetanilide of the formula

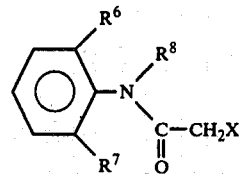

in which $R^6$ and $R^7$ are independently selected from the group consisting of hydrogen and $C_1$–$C_6$ alkyl, $R^8$ is a member selected from the group consisting of $C_1$–$C_6$ alkyl and -$R^9$-O-$R^{10}$, in which $R^9$ is $C_1$–$C_3$ alkylene and $R^{10}$ is $C_1$–$C_3$ alkyl, and X is chlorine, bromine, or iodine, in a weight ratio of amide to haloacetanilide of 0.01–10:1.

15. A method according to claim 14 in which $R^1$ is substituted phenyl, with one to three substituents independently selected from the group consisting of chlorine and methyl.

16. A method according to claim 14 in which $R^1$ is 3,5-dichlorophenyl or 3,5-dimethylphenyl.

17. A method according to claim 14 in which X is chlorine.

18. A method according to claim 14 in which said amide is N-(1,1-dimethyl-2-butynyl)-α-(3,5-dichlorophenoxy) butyramide and said haloacetanilide is N-[3'-methoxypropyl-(2)]-2-methyl-6-ethyl chloroacetanilide.

19. A method according to claim 14 in which said amide is N-(1,1-dimethyl-2-butynyl)-α-(3,5-dichlorophenoxy) butyramide and said haloacetanilide is N-methoxymethyl-2,6-diethyl chloroacetanilide.

20. A method according to claim 14 in which said amide is N-(1,1-dimethyl-2-butynyl)-α-(3,5-dichlorophenoxy) butyramide and said haloacetanilide is N-isopropyl chloroacetanilide.

21. A method according to claim 14 in which said amide is N-(1,1-dimethyl-2-butynyl)-α-(3,5-dimethylphenoxy) butyramide and said haloacetanilide is N-[3'-methoxypropyl-(2)]-2-methyl-6-ethyl chloroacetanilide.

22. A method according to claim 14 in which said amide is N-(1,1-dimethyl-2-butynyl)-α-(3,5-dimethylphenoxy) butyramide and said haloacetanilide is N-methoxymethyl-2,6-diethyl chloroacetanilide.

23. A method according to claim 14 in which said amide is N-(1,1-dimethyl-2-butynyl)-α-(3,5-dimethylphenoxy) butyramide and said haloacetanilide is N-isopropyl chloroacetanilide.

24. A method according to claim 14 in which said amide is N-(1,1-dimethyl-2-propynyl)-α-(3,5-dichlorophenoxy) butyramide and said haloacetanilide is N-[3'-methoxypropyl-(2)]-2-methyl-6-ethyl chloroacetanilide.

25. A method according to claim 14 in which said amide is N-(1,1-dimethyl-2-propynyl)-α-(3,5-dichlorophenoxy) butyramide and said haloacetanilide is N-methoxymethyl-2,6-diethyl chloroacetanilide.

26. A method according to claim 14 in which said amide is N-(1,1-dimethyl-2-propynyl)-α-(3,5-dichlorophenoxy) butyramide and said haloacetanilide is N-isopropyl chloroacetanilide.

* * * * *